(12) United States Patent
Ein-Gal

(10) Patent No.: US 7,014,361 B1
(45) Date of Patent: Mar. 21, 2006

(54) ADAPTIVE ROTATOR FOR GANTRY

(76) Inventor: Moshe Ein-Gal, 30 Azar Street, Ramat Hasharon 47203 (IL)

(*) Notice: Subject to any disclaimer, the term of this patent is extended or adjusted under 35 U.S.C. 154(b) by 0 days.

(21) Appl. No.: 11/126,156

(22) Filed: May 11, 2005

(51) Int. Cl.
*H05G 1/02* (2006.01)
(52) U.S. Cl. ........................ 378/197; 378/204
(58) Field of Classification Search .............. 378/4, 378/9, 15, 19, 64, 65, 193–197, 204; 250/370.08, 250/370.09; 600/425, 427
See application file for complete search history.

(56) References Cited

U.S. PATENT DOCUMENTS 5,912,943 A * 6/1999 Deucher et al. .......... 378/98.8
6,888,919 B1 * 5/2005 Graf ......................... 378/65

* cited by examiner

*Primary Examiner*—Edward J. Glick
*Assistant Examiner*—Courtney Thomas
(74) *Attorney, Agent, or Firm*—Dekel Patent Ltd.; David Klein

(57) ABSTRACT

An adaptive rotator including an at least partial ring mounted for rotation on a ring mount, the at least partial ring having provisions for mounting thereon accessories, a gantry coupler adapted to couple the at least partial ring to a rotatable gantry, and a mechanical compensator attached to at least one of the at least partial ring, the ring mount and the gantry coupler, the mechanical compensator yielding so that the at least partial ring rotates about a ring rotation axis generally collinear with a gantry rotation axis of the rotatable gantry without exercising significant forces on the rotatable gantry and the at least partial ring.

11 Claims, 4 Drawing Sheets

US 7,014,361 B1

ADAPTIVE ROTATOR FOR GANTRY

FIELD OF THE INVENTION

This invention relates generally to gantry systems, e.g., radiotherapy, radiosurgery and imaging systems, and particularly to an adaptive ring for mounting thereon accessories, such as but not limited to, imaging devices, wherein the adaptive ring rotates with the gantry.

BACKGROUND OF THE INVENTION

Some medical devices used for therapy or surgery, e.g., a linear accelerator (LINAC) or a cobalt teletherapy unit, or for imaging, e.g., CT scanners, incorporate a large gantry rotating about a patient. Upgrading older units (e.g., a LINAC), by adding imaging equipment on the rotating gantry would allow an efficient way to perform advanced treatments such as Image-Guided Radiotherapy (IGRT). However, mounting additional devices (e.g., collimators, radiation sources or imaging equipment) on the rotating gantry is limited due to the gantry's mechanical constraints.

LINAC manufacturers (e.g., Siemens, Varian, Electa, Tomotherapy) have introduced new devices designed to incorporate such additional imaging functions on the rotating gantry. Other manufacturers (e.g., BrainLabs, Accuray) utilize additional imaging equipment that is floor or ceiling-mounted.

SUMMARY OF THE INVENTION

The present invention seeks to provide an adaptive rotator, as is described more in detail hereinbelow, for mounting and rotating additional devices (such as imaging equipment) about a patient, in synchrony with a rotating gantry and without subjecting the gantry to excessive mechanical forces.

There is thus provided in accordance with an embodiment of the present invention an at least partial ring mounted for rotation on a ring mount, the at least partial ring having provisions for mounting thereon accessories, a gantry coupler adapted to couple the at least partial ring to a rotatable gantry, and a mechanical compensator attached to at least one of the at least partial ring, the ring mount and the gantry coupler, the mechanical compensator yielding so that the at least partial ring rotates about a ring rotation axis generally collinear with a gantry rotation axis of the rotatable gantry without exercising significant forces on the rotatable gantry and the at least partial ring. The at least partial ring may be elastically deformable.

In accordance with an embodiment of the present invention an image detector and fiducial markers with a known fixed location may be provided, wherein a misalignment between the ring rotation axis and the gantry rotation axis causes the fiducial markers to appear as shadows on an image captured by the image detector.

The ring mount may be mounted on a suspension device. Alternatively, the ring mount may be mounted on an adjustment device capable of moving the ring mount in any degree of freedom so as to align the ring rotation axis with the gantry rotation axis. A position sensor may cooperate with the adjustment device in a closed control loop.

An accessory may be mounted on the at least partial ring, such as an imaging device, a collimator, an x-ray source and/or an x-ray detector. A couch may be provided for positioning an object relative to the at least partial ring.

There is also provided in accordance with an embodiment of the present invention an Image-Guided Radiotherapy (IGRT) system including an at least partial ring mounted for rotation on a ring mount, the at least partial ring having provisions for mounting thereon accessories, the at least partial ring being coupled to a rotatable gantry by means of a gantry coupler, wherein at least one of the at least partial ring, the ring mount and the gantry coupler is adaptive so that the at least partial ring rotates about a ring rotation axis generally collinear with a gantry rotation axis of the rotatable gantry without exercising significant forces on the rotatable gantry and the at least partial ring, and an imaging device mounted on the at least partial ring adapted to provide images that guide movement of the gantry.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
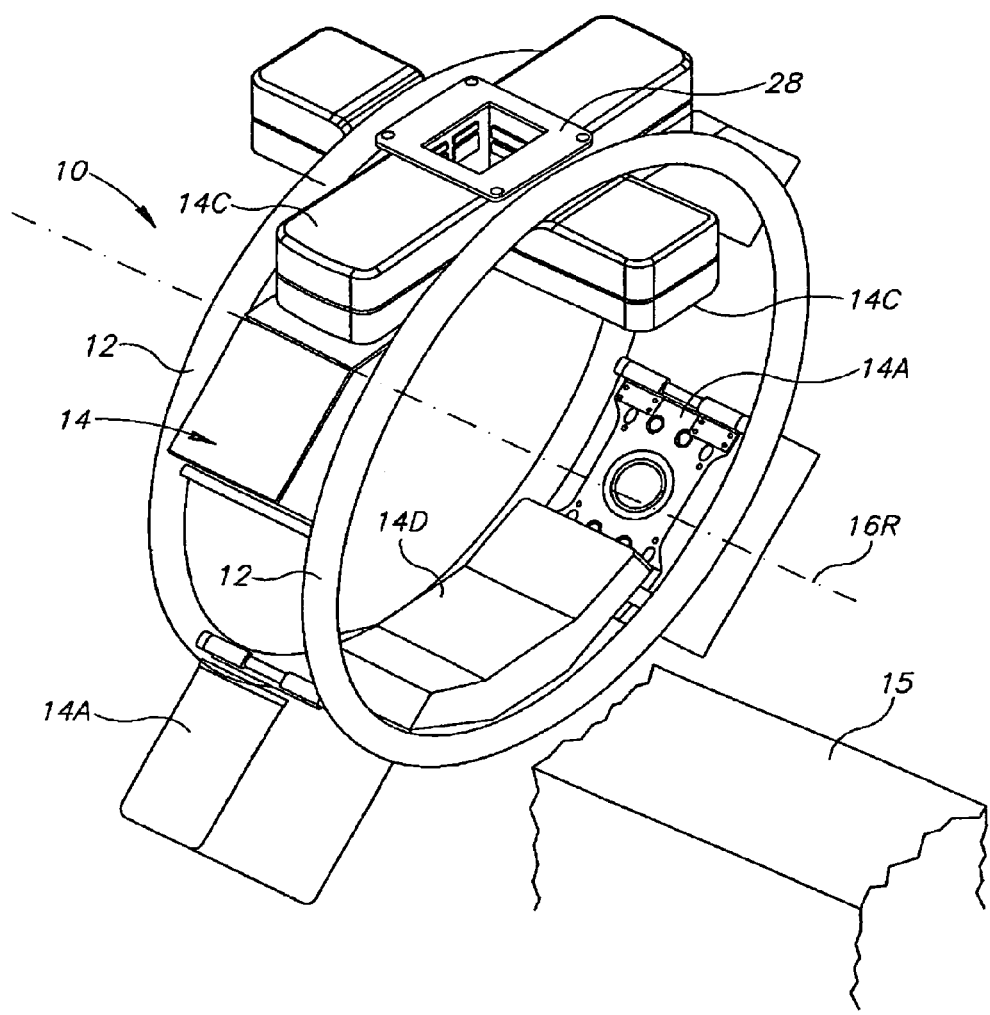
FIGS. 1 and 2 are simplified pictorial illustrations of an adaptive rotator, constructed and operative in accordance with an embodiment of the present invention.
Figure 2:
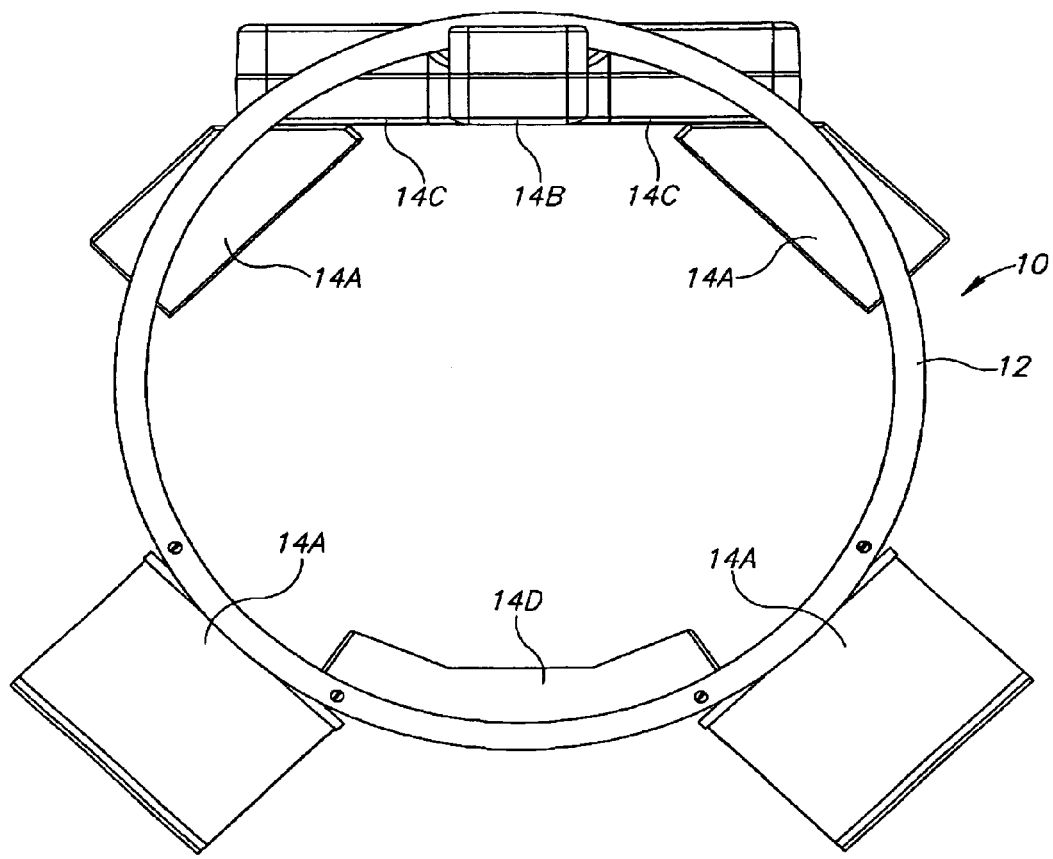

Reference is now made to FIGS. 1 and 2, which illustrate an adaptive rotator 10, constructed and operative in accordance with an embodiment of the present invention.

Adaptive rotator 10 may include an at least partial ring 12 (i.e., a full ring or a ring segment), on which accessories 14 may be mounted. In the illustrated embodiment, two axially spaced rings 12 are employed, but the invention is not limited to this arrangement. The at least partial ring 12 is arranged to rotate about a rotation axis 16R generally collinear with a rotation axis 16G of a rotatable gantry 18 (also referred to as a rotating gantry 18). Gantry 18 may be part of a medical device used for therapy or surgery, e.g., a linear accelerator (LINAC) or a cobalt teletherapy unit, or part of a medical device used for imaging, e.g., a CT scanner.

The accessories 14 that may be mounted on the at least partial ring 12 include, without limitation, one or more imaging devices 14A (e.g., a portal image detector), a collimator 14B, an x-ray source 14C and an x-ray detector 14D and any combination thereof. A couch (or support table) 15 may be provided for positioning an object (e.g., patient) relative to the at least partial ring 12 (FIG. 1).

Figure 3:
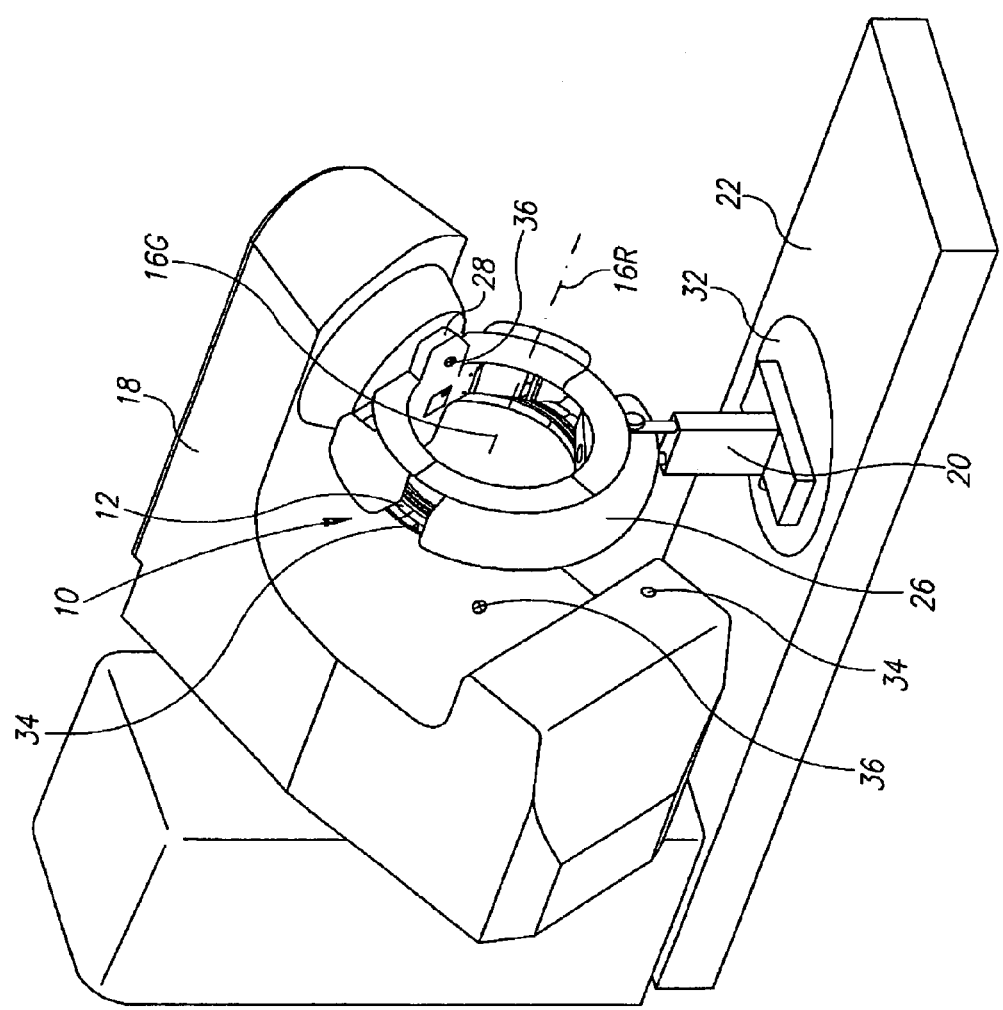
FIG. 3 is a simplified pictorial illustration of the adaptive rotator connected to a gantry of a medical device, in accordance with an embodiment of the present invention.
Figure 4:
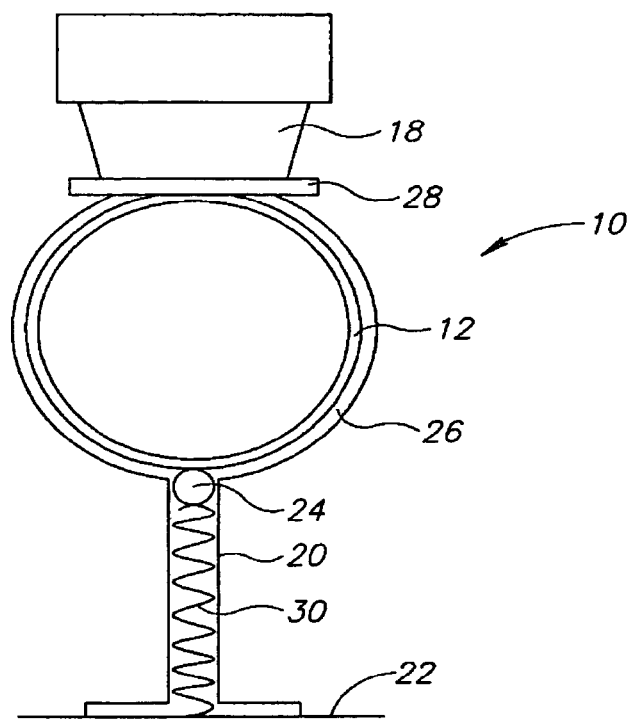
FIG. 4 is a simplified front view illustration of the adaptive rotator connected to the gantry.

Reference is now made to FIGS. 3 and 4. The at least partial ring 12 may be mounted for rotation on a ring mount 20, which may be attached to a mounting surface 22, e.g., floor, turntable, wall or ceiling (or adjustment device described below). "Mounted for rotation" includes any bearing(s) or journal(s) that support the weight of the at least partial ring 12 and the accessories 14 and enable rotational motion of the at least partial ring 12 with respect to the ring mount 20. For example, without limitation, the at least partial ring 12 may be supported by one or more bearing elements 24 (e.g., roller bearings or ball bearings and the like, seen in FIG. 4), housed in a ring housing 26 that at least partially encloses the at least partial ring 12. Another example of suitable bearing elements 24 is hydrostatic bearings, e.g., bearing pads that support the load thereupon and permit rotation with pressurized fluid (e.g., oil). Hydrostatic lubrication provides extremely low coefficients of friction and very steady rotation.

The at least partial ring 12 may be secured to the rotatable gantry 18 by a gantry coupler 28, such as but not limited to, a mounting plate with mounting holes or screws situated near collimator 14B. The at least partial ring 12 is thus mechanically attached to two independent objects: via the gantry coupler 28 to the rotating gantry 18 and via the ring mount 20 to the mounting surface 22. The at least partial ring 12 is not perfectly circular and the respective rotation axes of the rotating gantry and the ring are not perfectly collinear. Since the double-attachment should be maintained for various rotation angles, the assembly made of the ring 12, ring mount 20 and gantry coupler 28 may become mechanically over-constrained if the three are all mechanically rigid objects.

The present invention circumvents this difficulty by adding one or more mechanical compensators to the assembly made of the at least partial ring 12, ring mount 20 and gantry coupler 28 to be adaptive. Throughout the specification and claims, the term "adaptive" encompasses the ability to vary geometry and/or spatial position in order to conform to the double-attachment constraints, or the ability to provide corrective information and/or measures for compensating for the double-attachment constraints.

One example of an adaptive arrangement (that is, mechanical compensator) is to mount ring mount 20 on a suspension device 30, such as but not limited to, one or more springs (with or without constant spring force), dampers, vibration mounts, shock mounts and any combination thereof. The suspension device 30 may compensate for the imprecise alignment of the at least partial ring 12 and gantry 18, thereby enabling the at least partial ring 12 to rotate simultaneously with gantry 18 without exercising significant forces on the gantry 18 or the at least partial ring 12.

Another example of an adaptive arrangement is to mount ring mount 20 on a driver or adjustment device 32, such as but not limited to, a platform that is capable of moving the ring mount 20 in any degree of freedom (translational or rotational) for fine tuning the alignment of the at least partial ring 12 with respect to the gantry 18 so as to align the ring rotation axis 16R with gantry rotation axis 16G. The adjustment device 32 may include, without limitation, a turntable, hydraulic or pneumatic (or electric) lift capable of translating and/or rotating the ring mount 20 and any combination thereof.

As a particular non-limiting example, the adjustment device 32 may move ring mount 20 with respect to the gantry 18 by means of a position sensor 34 that cooperates with adjustment device 32 in a closed control loop. In general, the position sensor 34 may comprise, without limitation, accelerometers, proximity sensors, encoders, CT scanners, x-ray fluoroscopes, ultrasound scanners, portal imagers and viewing devices, such as CCTV or CCD cameras, and many others and any combination thereof. The position sensor 34 may sense the position of the ring mount 20, at least partial ring 12 and/or gantry 18, and thereby sense the relative alignment of rotation axis 16R with rotation axis 16G. The sensed information may be passed on to a controller (not shown) in operative communication with adjustment device 32. The controller uses the sensed information to instruct adjustment device 32 to modify the position of ring mount 20 to compensate for the sensed imperfections.

As mentioned above, the at least partial ring 12 is operable to carry the weight of the accessories 14 while being slightly distorted (elastically deformable) in order to comply with the double-attachment. The deformation may change with various rotation angles, and images obtained by ring-mounted imaging devices are corrected when used for target localization. In accordance with one non-limiting embodiment of the present invention, fiducial markers 36 may be rigidly attached with known geometry to a portion of the gantry system, e.g., to a radiation head or a collimator. Alternatively or additionally, fiducial markers 36 may be opposite the portal image detector 14A, or between x-ray source 14C and x-ray detector 14D or on collimator 14C. As the gantry 18 rotates, the at least partial ring 12 also rotates, but as mentioned before, there may be a non-perfect alignment between the two and the at least partial ring 12 may rotate with some deviation from the gantry 18. This deviation causes the fiducial markers 36 to appear as shadows on an image captured by the imaging equipment. The location of the shadows allows precise image registration in the collimator coordinate system. An image processor 38 may be provided for deriving the localization data for the image registration.

The gantry coupler 28 may include a coupling with sufficient flexibility and resilience that yields, compensates and "gives in" to tolerance discrepancies, sagging, and any other causes for misalignment between the at least partial ring 12 and gantry 18, so that the at least partial ring 12 and gantry 18 are not subjected to excessive forces. Such a coupling may include, without limitation, torsional springs.

The adaptive rotator 10, working in conjunction with imaging devices 14, provides an efficient way to perform advanced treatments such as Image-Guided Radiotherapy (IGRT).

Figure 5:
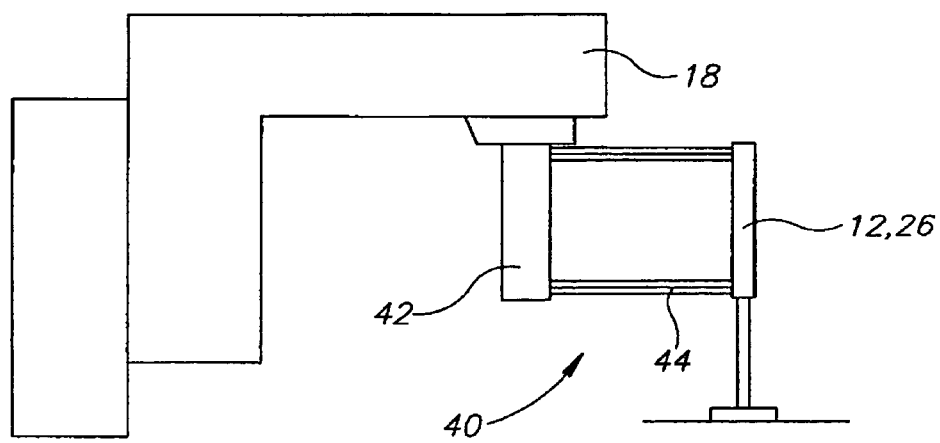
FIG. 5 is a simplified side view illustration of the adaptive rotator connected to the gantry with a coupler, in accordance with an embodiment of the present invention.

Reference is now made to FIG. 5, which illustrates the adaptive rotator 10 connected to gantry 18 with a coupler 40, in accordance with an embodiment of the present invention. Coupler 40 may include an auxiliary ring 42 attached by axial links 44 (e.g., bars or rods) to ring mount 20. Axial links 44 may be rigid or flexible. Coupler 40 increases the possibilities of placing a patient through the ring mount 20 with respect to the gantry 18.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. An adaptive rotator comprising:
    an at least partial ring mounted for rotation on a ring mount, said at least partial ring having provisions for mounting thereon accessories;
    a gantry coupler adapted to couple said at least partial ring to a rotatable gantry; and
    a mechanical compensator attached to at least one of said at least partial ring, said ring mount and said gantry coupler, said mechanical compensator yielding so that said at least partial ring rotates about a ring rotation axis generally collinear with a gantry rotation axis of the rotatable gantry without exercising significant forces on the rotatable gantry and said at least partial ring.

2. The adaptive rotator according to claim 1, wherein said at least partial ring is elastically deformable.

3. The adaptive rotator according to claim 1, further comprising an image detector and fiducial markers with a known fixed location, wherein a misalignment between the ring rotation axis and the gantry rotation axis causes the fiducial markers to appear as shadows on an image captured by the image detector.

4. The adaptive rotator according to claim 1, wherein said mechanical compensator comprises a suspension device on which said ring mount is mounted.

5. The adaptive rotator according to claim 1, wherein said mechanical compensator comprises an adjustment device on which said ring mount is mounted, capable of moving the ring mount in any degree of freedom so as to align the ring rotation axis with the gantry rotation axis.

6. The adaptive rotator according to claim 5, further comprising a position sensor that cooperates with said adjustment device in a closed control loop.

7. The adaptive rotator according to claim 6, wherein said position sensor comprises at least one of an accelerometer, a proximity sensor, an encoder, a CT scanner, an x-ray fluoroscope, an ultrasound scanner, a portal imager and a viewing device.

8. The adaptive rotator according to claim 1, further comprising an accessory mounted on said at least partial ring, said accessory comprising at least one of an imaging device, a collimator, an x-ray source and an x-ray detector.

9. The adaptive rotator according to claim 1, further comprising a couch for positioning an object relative to said at least partial ring.

10. The adaptive rotator according to claim 1, further comprising a rotatable gantry operable to carry a radiation source.

11. An Image-Guided Radiotherapy (IGRT) system comprising:
- an at least partial ring mounted for rotation on a ring mount, said at least partial ring having provisions for mounting thereon accessories, said at least partial ring being coupled to a rotatable gantry by means of a gantry coupler, and a mechanical compensator attached to at least one of said at least partial ring, said ring mount and said gantry coupler, said mechanical compensator yielding so that said at least partial ring rotates about a ring rotation axis generally collinear with a gantry rotation axis of the rotatable gantry without exercising significant forces on the rotatable gantry and said at least partial ring; and
- an imaging device mounted on said at least partial ring adapted to provide images that guide movement of said gantry.

* * * * *